United States Patent [19]
Borders

[11] Patent Number: 6,096,025
[45] Date of Patent: Aug. 1, 2000

[54] MOBILE SURGICAL SUPPORT APPARATUS

[75] Inventor: Richard L. Borders, Cincinnati, Ohio

[73] Assignee: Hill-Rom, Inc., Batesville, Ind.

[21] Appl. No.: 09/187,945

[22] Filed: Nov. 6, 1998

Related U.S. Application Data

[60] Provisional application No. 60/064,709, Nov. 7, 1997.

[51] Int. Cl.[7] .................................................. A61B 17/00
[52] U.S. Cl. .................................................. 606/1; 606/10
[58] Field of Search .................................. 606/1, 10, 11, 606/12; 312/246

[56] References Cited

U.S. PATENT DOCUMENTS

| | | |
|---|---|---|
| D. 331,621 | 12/1992 | Tapolcai . |
| 3,769,502 | 10/1973 | Schultz et al. . |
| 4,498,693 | 2/1985 | Schindele . |
| 4,646,211 | 2/1987 | Gallant et al. . |
| 4,662,524 | 5/1987 | Fullenkamp et al. . |
| 4,720,768 | 1/1988 | Schindele . |
| 4,807,659 | 2/1989 | Schindele . |
| 4,821,470 | 4/1989 | Kappers et al. . |
| 5,060,425 | 10/1991 | Kappers et al. . |
| 5,072,906 | 12/1991 | Foster . |
| 5,077,843 | 1/1992 | Foster et al. . |
| 5,107,636 | 4/1992 | Schindele et al. . |
| 5,117,521 | 6/1992 | Foster et al. . |
| 5,186,337 | 2/1993 | Foster et al. . |
| 5,284,255 | 2/1994 | Foster et al. . |
| 5,299,338 | 4/1994 | Foster . |
| 5,318,516 | 6/1994 | Cosmescu ................................ 606/10 |
| 5,335,651 | 8/1994 | Foster et al. . |
| 5,336,218 | 8/1994 | Linhares ...................................... 606/10 |
| 5,337,845 | 8/1994 | Foster et al. . |
| 5,370,111 | 12/1994 | Reeder et al. . |
| 5,398,359 | 3/1995 | Foster . |
| 5,452,807 | 9/1995 | Foster et al. . |
| 5,455,975 | 10/1995 | Foster . |
| 5,457,831 | 10/1995 | Foster et al. . |
| 5,497,766 | 3/1996 | Foster et al. . |
| 5,618,090 | 4/1997 | Montague et al. . |
| 5,748,767 | 5/1998 | Raab .......................................... 606/1 |
| 5,756,933 | 5/1998 | Pitchford et al. . |
| 5,788,688 | 8/1998 | Bauer et al. ............................... 606/1 |

FOREIGN PATENT DOCUMENTS

| 96/35403 | 11/1996 | WIPO . |
|---|---|---|
| WO 96/35403 | 11/1996 | WIPO . |

*Primary Examiner*—Linda C. M. Dvorak
*Assistant Examiner*—Sonya Harris-Ogugua
*Attorney, Agent, or Firm*—Barnes & Thornburg

[57] ABSTRACT

A surgical support apparatus includes a mobile support station configured to receive medical equipment thereon. The mobile support station includes at least one gas outlet and at least one electrical outlet for supplying gas and electricity to an operating room. The apparatus also includes a flexible umbilical line having a first end coupled to the mobile support station and a second end configured to be coupled to a ceiling of the operating room. The umbilical line is configured to route medical gases and electrical lines from a gas supply and an electrical power supply, respectively, through the ceiling and to the mobile support station.

10 Claims, 4 Drawing Sheets

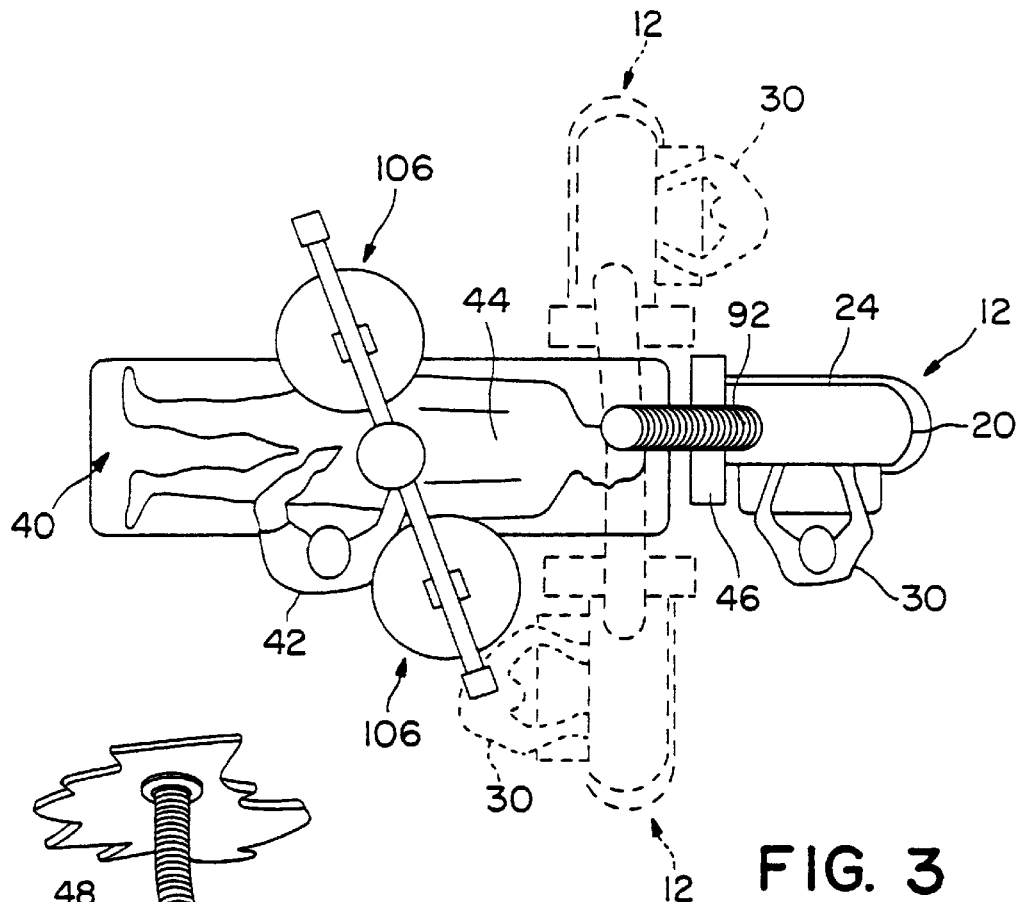
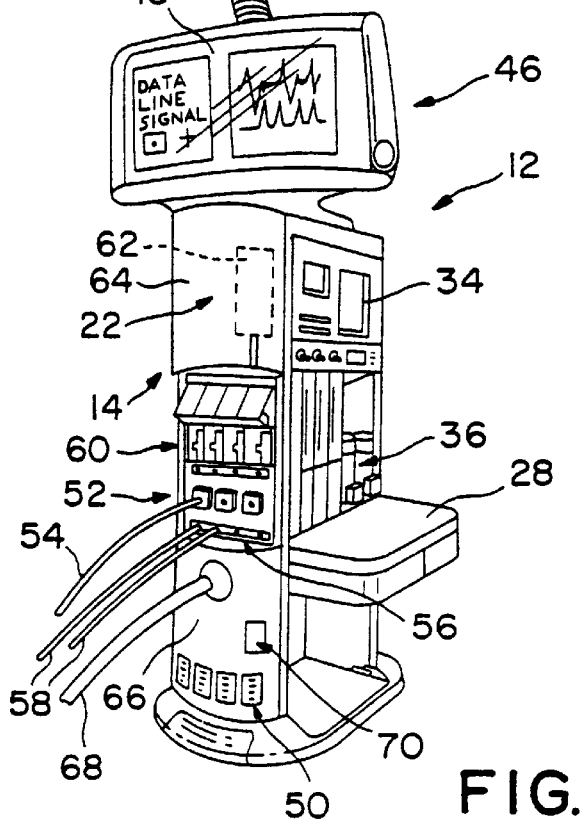
FIG. 3
FIG. 2

MOBILE SURGICAL SUPPORT APPARATUS

This application claims the benefit of U.S. provisional application Ser. No. 60/064,709 filed Nov. 7, 1997.

BACKGROUND AND SUMMARY OF THE INVENTION

The present invention relates to a mobile surgical support apparatus. More particularly, the present invention relates to a free-standing surgical support apparatus which integrates key surgical support needs and technologies in one central area in an operating room.

The mobile surgical apparatus includes a movable support station configured to receive medical equipment items such as anesthesiology equipment, IV pumps and IV pre-warming devices, a patient thermal regulation apparatus, a central monitor, and a controller for various equipment. The mobile surgical support station is also configured to provide gas and electrical output to the operating room to support the surgical procedure. The mobile support station further supplies electrical power and fluid to control the surgical table or a support surface located on the surgical table. The mobile surgical station further provides a data link to the communication network of the hospital to provide transient information and data between the network from the mobile support station. Other medical equipment located on the mobile support station may illustratively include electric outlets for cauterizing surgical tools and a driver for a surgeon's fiber optic head light.

The mobile surgical support apparatus is movable to different locations in the operating room depending upon surgical needs. Electrical power, gases, and communication links are provided through a flexible umbilical line coupled to a ceiling of the operating room. The umbilical line is coupled directly to the ceiling in one embodiment of the present invention. In another embodiment of the present invention, the umbilical line is coupled to a boom which is rotatable about a pivot axis. The flexible umbilical line permits the mobile surgical support station to be moved to different locations within the operating room while still supplying the electrical power, medical gases, and communication links.

The mobile surgical support apparatus of the present invention centralizes key patient support technologies in the operating room. The apparatus saves floor space by consolidating equipment on to a single mobile support station. This reduces confusion and clutter of having separate equipment on separate stands or on the floor. All support functions are easily accessible by the caregiver. Separate IV stands are not required with the mobile surgical apparatus of the present invention. There is no requirement for heavy duty ceiling support structures since the weight of the mobile surgical apparatus is not supported by the ceiling.

Additional features of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying drawings in which:

FIG. 2 is a perspective view illustrating additional features of the mobile surgical support apparatus;

FIG. 3 is a top plan view of an operating room layout, illustrating various positions of the mobile surgical support apparatus within the operating room;

DETAILED DESCRIPTION OF THE DRAWINGS

Figure 1:
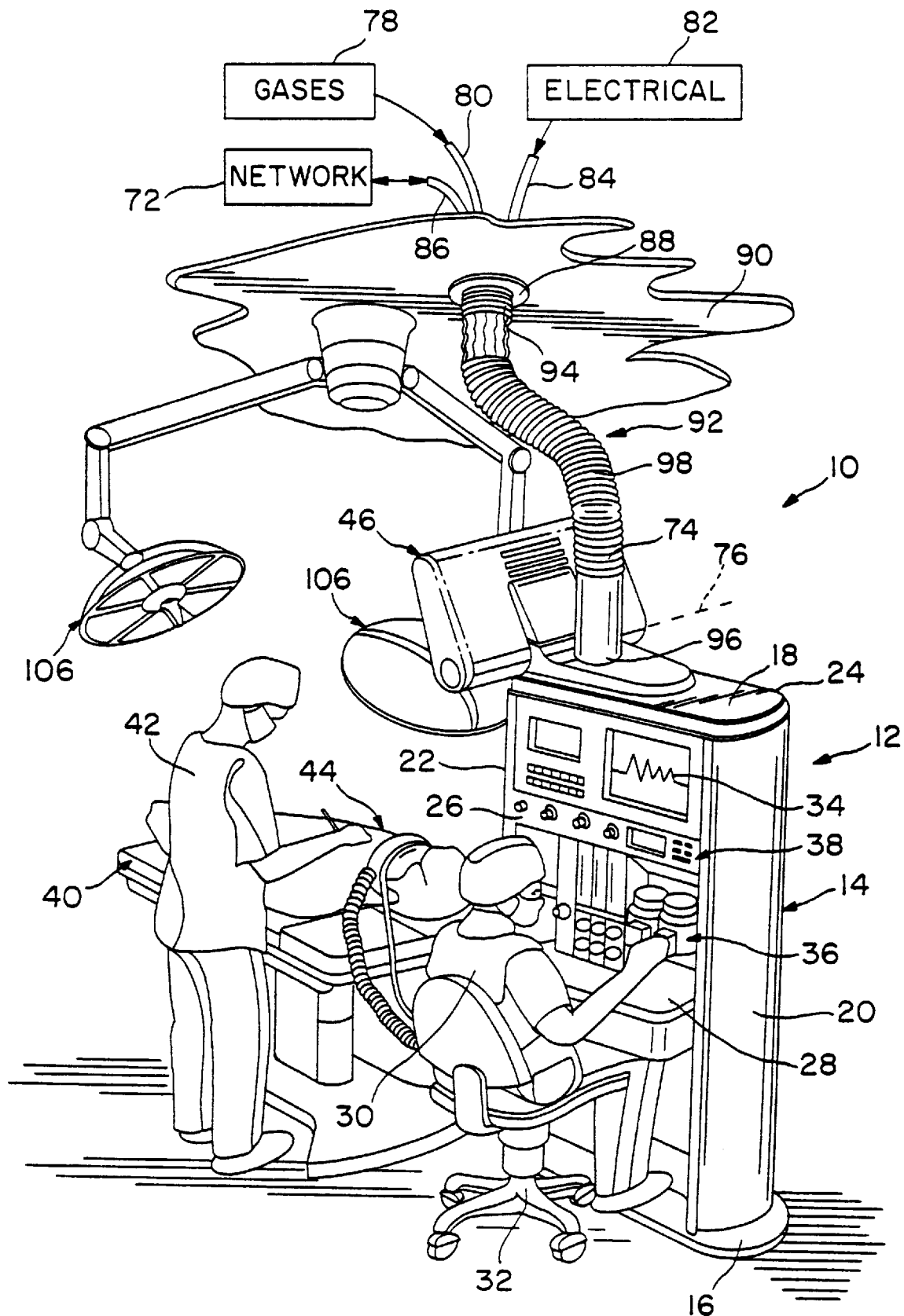
FIG. 1 is a perspective view of a mobile surgical support apparatus of the present invention.

Referring now to the drawings, FIG. 1 illustrates a mobile surgical support apparatus 10 of one embodiment of the present invention. The apparatus 10 includes a mobile surgical support station 12 having a plurality of casters and a suitable braking mechanism. Therefore, the mobile surgical support station 12 can be moved to desired locations within an operating room and then casters can be locked to prevent movement of the station 12 during a surgical procedure.

The mobile surgical support station 12 includes a housing 14 having a base 16, a top 18, side portions 20 and 22, and a rear wall 24. A pair of shelves 26 and 28 are configured to support various items needed for surgical procedures in an operating room. A caregiver such as an anesthesiologist 30 therefore has ready access to key surgical support equipment in one convenient location. Illustratively, the anesthesiologist 30 can sit on chair 32 adjacent the mobile surgical support station 12 to operate the equipment.

As shown in FIG. 1, the mobile surgical support station 12 includes a first monitor 34 for use by caregiver 30. Anesthesia equipment such as vaporizers 36 is also located on the mobile surgical support station 12. Controls and drivers 38 for various surgical support equipment are also located on the mobile surgical support station 12. The controls 38 may be hand or voice actuated. Outlets are provided on the mobile surgical support station 12 for electric cauterizing surgical equipment and for driving a surgeon's fiber optic head light.

Additional surgical support equipment is located along side 22 of mobile surgical support station 12 facing toward the surgical table 40 where a surgeon 42 is working on a patient 44. As shown in FIG. 2, a central monitor 46 includes a display screen 48 to provide information to the surgeon 42. The mobile surgical support station 12 includes electrical outlets 50 to supply electrical power from a power supply 82 as needed to the operating room. The mobile surgical support station 12 further includes a plurality of gas outlets 52 configured to be coupled to gas supply lines 54 and IV outlets 56 for routing IV lines 58 to the patient. Gas outlets 52 are coupled to gas supply lines 80 as discussed below.

IV pumps 60 are located within a recess in the side 22 of the mobile surgical support station 12. IV bags 60 are located on mobile surgical support station 12 above the pumps 60. The IV lines 58 may be routed through a pre-warmer, which may be a separate pre-warming device or which may be a pre-warming device located in a control apparatus 66 coupled to mobile surgical support station 12.

The control apparatus 66 functions to pre-warm the fluid in the IV lines 58. In addition, the control apparatus 66 supplies fluid through tube 68 to provide thermal regulation for the patient, or to control a support surface or other therapy device on the surgical table 40. Details of the control apparatus 66 are disclosed in U.S. application Ser. No. 09/187,989, entitled PATIENT THERMAL REGULATION APPARATUS, filed Nov. 6, 1998 (Attorney Docket 7175-60104) which is incorporated herein by reference.

Mobile surgical support station 12 further includes a communication network connection 70 for coupling equipment in the operating room to the hospital network 72. The monitor 46 on top surface 18 of mobile surgical support station 12 is rotatable about a vertical axis 74. Display 48 is also pivotable about axis 76. Therefore, the orientation of display 48 can be adjusted depending upon the particular preferences of the surgeon 42. A video camera is also included on mobile support station 12. Monitor 46 and the camera permit telesurgery procedures to be implemented over communication lines 86.

Medical gases from a gas supply 78 are supplied to the mobile surgical support station 12 by supply lines 80. Illustratively, gases supplied through lines 80 include oxygen, air, nitrous oxide, nitrogen, carbon dioxide, helium, and vacuum. Electrical power from electrical power supply 82 is supplied to the mobile surgical support station 12 through a supply line 84. The mobile surgical support station 12 is also coupled to the communication network 72 by supply line 86.

The supply lines 80, 84, and 86 extend through an opening 88 formed in a ceiling 90 in the operating room. The supply lines 80, 84, and 86 extend through a flexible umbilical line 92 having a first end 94 coupled to the opening 88 in the ceiling 90 by a swivel connection. A second end 96 of umbilical line 92 is coupled to the mobile surgical support station 12. An interior region 98 of umbilical line 92 is segmented into separate sections to isolate the lines 80, 84, and 86. Since umbilical line 92 is flexible, the mobile surgical support station 12 can be moved to various positions within the operating room as best illustrated in FIG. 3. The opening 88 in ceiling 90 can be located at any desired location. Substantial reinforcement is not required in ceiling 90 to support umbilical line 92. The weight of the mobile support station 12 is supported on the ground and not the ceiling 90.

Figure 4:
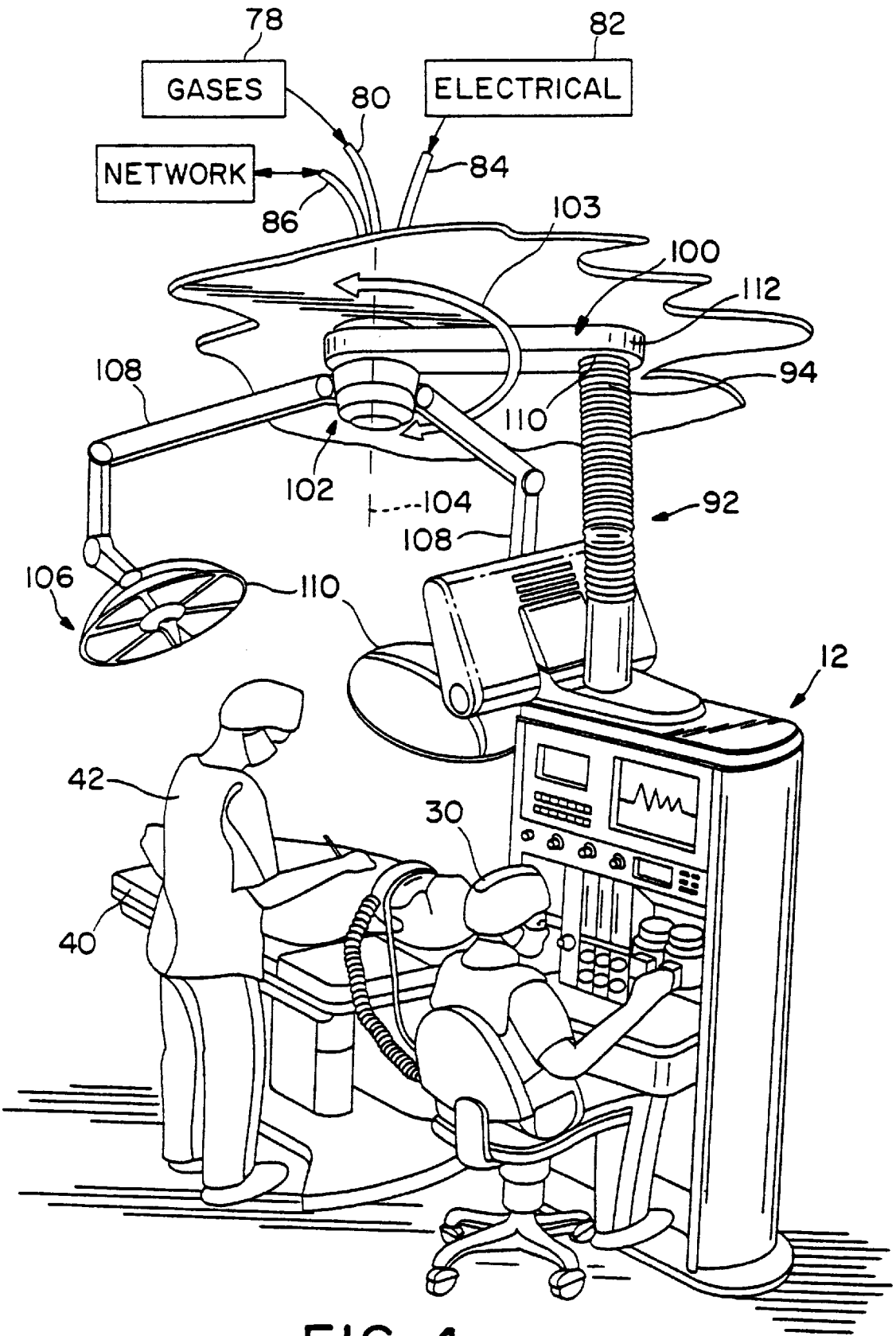
FIG. 4 is a perspective view of another embodiment of the present invention in which a flexible umbilical line for routing gases, electrical power, and communication network data lines to the mobile surgical support apparatus are passed through a movable boom pivotably coupled to the ceiling.
Figure 5:
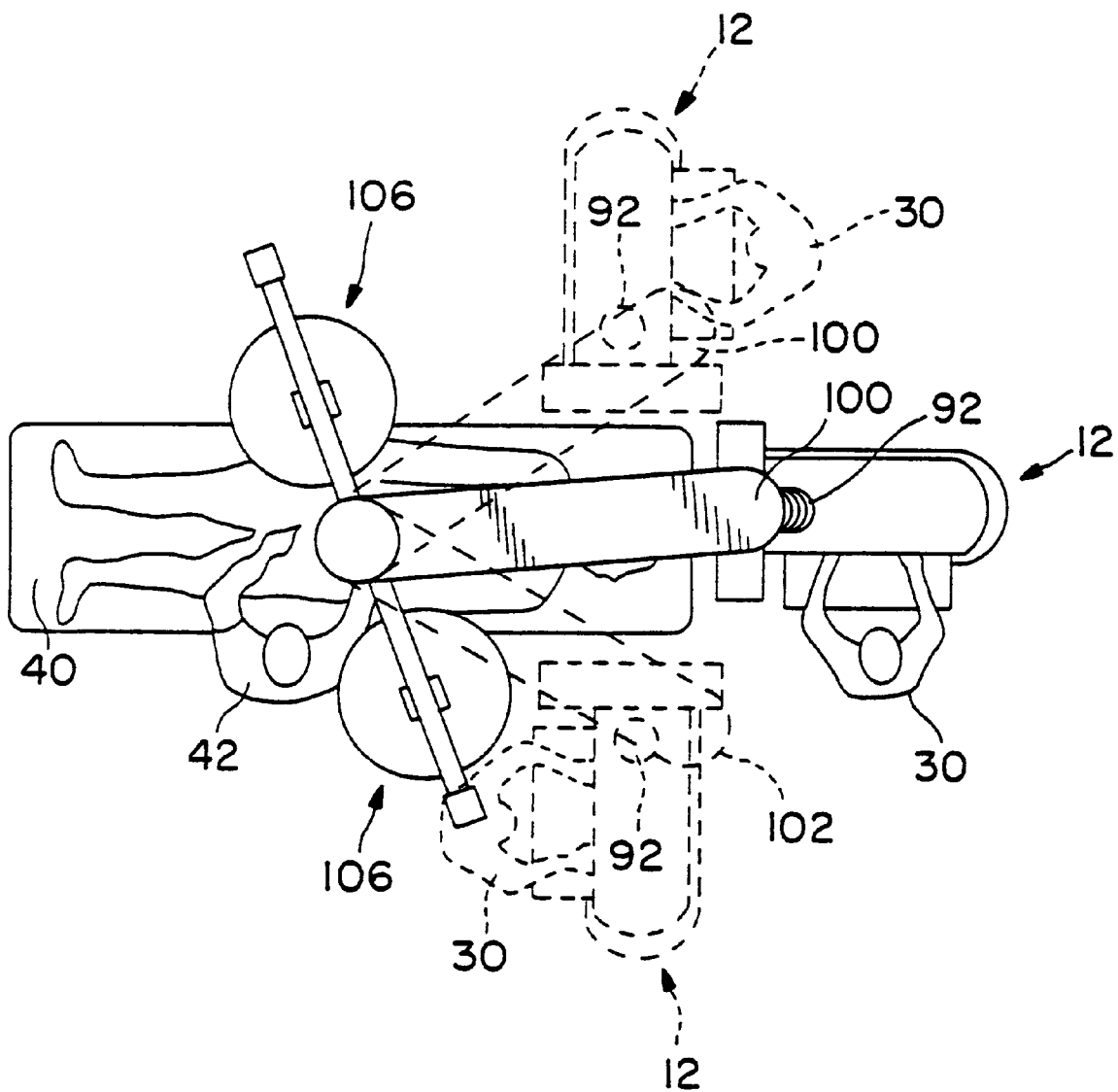
FIG. 5 is a top view of the operating room layout illustrating a plurality of different positions for the mobile surgical support apparatus of FIG. 4 around a surgical table.

FIGS. 4 and 5 illustrate another embodiment of the present invention. In this embodiment, a hollow boom 100 is coupled to a central hub 102 coupled to ceiling 90. Boom 100 is configured to rotate about pivot axis 104 of the hub 102 in the direction of double headed arrow 103. Illustratively, surgical lights 106 are also coupled to the hub 102. Surgical lights 106 include support arms 108 which are also rotatably mounted on the hub 102. Surgical lightheads 110 are coupled to opposite ends of the support arms 108.

The supply lines 80, 84, and 86 are routed through the ceiling 90 and hub 106 and then through boom 100. The first end 94 of umbilical line 92 is coupled to an aperture 110 formed at distal end 112 of boom 100. The boom 100 has a sufficient length so that the umbilical line 92 does not interfere with movement of the surgical lights 106. FIG. 5 illustrates movement of the mobile surgical support station 12 to various locations using the boom 100.

Although the invention has been described in detail with reference to a certain illustrated embodiment, variations and modifications exist within the scope and spirit of the invention as described and as defined in the following claims.

What is claimed is:

1. A surgical support apparatus comprising:

a mobile support station configured to receive medical equipment thereon, the mobile support station including at least one gas outlet and at least one electrical outlet for supplying gas and electricity to an operating room; and an umbilical line having a first end coupled to the mobile support station and a second end configured to be coupled to a ceiling of the operating room, the umbilical line being configured to route medical gas lines and electrical lines from a gas supply and an electrical power supply, respectively, through the ceiling and to the mobile support station, the umbilical line being flexible along a majority of its length between the first end and the second end.

2. The apparatus of claim 1, further comprising a boom having a first end pivotably coupled to the ceiling about a pivot axis and a second end coupled to the second end of the umbilical line, the medical gases and electrical lines being routed through the boom and the umbilical line to the mobile support station.

3. The apparatus of claim 1, wherein the mobile support station includes at least one of anesthesiology equipment, an IV pump, an IV pre-warmer, and a patient thermal regulation controller.

4. The apparatus of claim 1, wherein the mobile support station includes a monitor for monitoring a condition of the patient.

5. The apparatus of claim 1, further comprising a communication line extending through the ceiling and the umbilical line to the mobile support station to provide a link to a communication network on the mobile support station.

6. The apparatus of claim 1, wherein the mobile support station includes a plurality of casters and a braking mechanism.

7. The apparatus of claim 1, wherein the mobile support station includes a top surface having a monitor located thereon, the monitor being rotatable about a generally vertical first axis and pivotable about a second axis generally transverse to the first axis.

8. The apparatus of claim 1, wherein the medical gases include at least one of oxygen, air, nitrous oxide, nitrogen, carbon dioxide, helium, and vacuum.

9. The apparatus of claim 1, wherein the mobile support station includes an outlet for energizing electrical cauterizing tools.

10. The apparatus of claim 1, wherein the mobile support station includes a driver configured to be coupled to a fiber optic light source.

* * * * *